United States Patent
Moen et al.

(10) Patent No.: US 9,232,790 B2
(45) Date of Patent: Jan. 12, 2016

(54) ANTIMICROBIAL CLEANSING COMPOSITIONS

(75) Inventors: Helen Kathleen Moen, Hortonville, WI (US); Corey Thomas Cunningham, Larsen, WI (US); Douglas R. Hoffman, Oshkosh, WI (US); Scott W. Wenzel, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 230 days.

(21) Appl. No.: 13/196,313

(22) Filed: Aug. 2, 2011

(65) Prior Publication Data

US 2013/0035396 A1    Feb. 7, 2013

(51) Int. Cl.
*A01N 33/12* (2006.01)
*A01P 1/00* (2006.01)

(52) U.S. Cl.
CPC ...................................... *A01N 33/12* (2013.01)

(58) Field of Classification Search
CPC .... A01N 33/12; A01N 25/30; A01N 2300/00
USPC ........................................................ 424/478
See application file for complete search history.

(56) References Cited

U.S. PATENT DOCUMENTS

| | | | |
|---|---|---|---|
| 5,292,528 A | 3/1994 | Mori et al. | |
| 5,681,802 A | 10/1997 | Fujiwara et al. | |
| 5,730,963 A | 3/1998 | Hilliard, Jr. et al. | |
| 5,925,615 A | 7/1999 | Kern et al. | |
| 6,383,505 B1 | 5/2002 | Kaiser et al. | |
| 6,383,997 B1 | 5/2002 | McManus | |
| 6,610,315 B2 | 8/2003 | Scholz et al. | |
| 6,616,922 B2 * | 9/2003 | Taylor et al. | 424/70.28 |
| 6,897,253 B2 | 5/2005 | Schmucker-Castner et al. | |
| 7,517,842 B2 | 4/2009 | Barnhart et al. | |
| 7,838,477 B2 | 11/2010 | Wenzel et al. | |
| 7,842,232 B2 | 11/2010 | Bosch et al. | |
| 7,985,773 B2 | 7/2011 | Greten et al. | |
| 2003/0185869 A1 | 10/2003 | Wertz et al. | |
| 2005/0048008 A1 | 3/2005 | Gupta | |
| 2005/0084454 A1 | 4/2005 | Fust | |
| 2005/0271595 A1 | 12/2005 | Brown | |
| 2006/0173709 A1 | 8/2006 | Traynor et al. | |
| 2007/0179207 A1 | 8/2007 | Fernandez de Castro et al. | |
| 2008/0194532 A1 | 8/2008 | Rabinovich-Guilatt et al. | |
| 2008/0199535 A1 | 8/2008 | Taylor et al. | |
| 2008/0241070 A1 | 10/2008 | Ryde et al. | |
| 2009/0156451 A1 | 6/2009 | Seidling et al. | |
| 2009/0226498 A1 | 9/2009 | Flugge-Berendes et al. | |
| 2009/0262597 A1 | 10/2009 | Kieffer et al. | |
| 2009/0324505 A1 | 12/2009 | Seidling et al. | |
| 2011/0144214 A1 * | 6/2011 | Snyder et al. | 514/724 |
| 2012/0070341 A1 * | 3/2012 | Eder et al. | 422/28 |

FOREIGN PATENT DOCUMENTS

| | | |
|---|---|---|
| KR | 20020023902 A | 3/2002 |
| WO | 2004024779 A2 | 3/2004 |
| WO | 2010039291 A1 | 4/2010 |
| WO | 2010089228 A1 | 8/2010 |
| WO | 2011124241 A2 | 10/2011 |

OTHER PUBLICATIONS

P. Deluca, H. Kostenbauder, Interaction of preservatives with macromolecules IV. Binding of quaternary ammonium compounds by nonionic agents, Journal of the American Pharmaceutical Association 49 (7) 430-437 (1960).
International Search Report and Written Opinion for PCT/IB2012/053173 dated Feb. 25, 2013.

* cited by examiner

*Primary Examiner* — Anoop Singh
*Assistant Examiner* — Doan Phan
(74) *Attorney, Agent, or Firm* — Armstrong Teasdale LLP

(57) ABSTRACT

Antimicrobial cleansing compositions are disclosed. The cleansing compositions include thin liquid/foaming compositions and gels. The antimicrobial cleansing compositions are effective antimicrobials and safe for everyday use.

23 Claims, No Drawings

ANTIMICROBIAL CLEANSING COMPOSITIONS

BACKGROUND OF THE DISCLOSURE

The present disclosure relates generally to cleansing compositions. More particularly, the present disclosure is directed to antimicrobial cleansing compositions such as hand cleansing foams and gel soaps. The antimicrobial cleansing compositions avoid the use of potentially hazardous and/or environmentally dangerous ingredients, the use of which are recently being increasingly limited in cleansing compositions by governmental bodies and regulatory agencies.

Cleansing compositions commonly contain antimicrobial actives that, while being effective, have recently been found to be potentially environmentally dangerous ingredients. More particularly, many regulatory agencies and consumer groups have raised issues regarding the use of these potentially dangerous ingredients, and in particular, have raised issues regarding the use of ingredients such as triclosan, triclocarban and halogenated phenols. For example, many governmental bodies and regulatory agencies are more commonly requiring registration of individual raw materials, which results in cost increases and product release delays. Similarly, the European Union is in the process of imposing a new regulation on the classification, labeling, and packaging of substances and mixtures, which will replace the Dangerous Substances Directive and the Dangerous Preparations Directive (DSD/DPD) currently in place. These regulations include assessments of individual ingredients along with combinations based on hazard classification.

Because of these regulations and concerns over the use of these potentially hazardous and environmentally dangerous ingredients, there exists a need to develop alternative antimicrobial cleansing compositions containing active ingredients that are effective and safe for everyday use.

SUMMARY OF THE DISCLOSURE

The present disclosure relates generally to cleansing compositions, including hand cleansing foams and gel washes. The antimicrobial cleansing compositions avoid the use of potentially environmentally dangerous ingredients that may require the filing of hazard and precautionary statements.

In one aspect, the present disclosure is directed to an antimicrobial cleansing composition including a polar carrier solvent, a cationic compatible surfactant, a quaternary ammonium biocide, and a cationic compatible afterfeel agent. The cleansing composition includes from about 0.1% (w/w) to about 15% (w/w) cationic compatible surfactant and from about 0.01% (w/w) to about 10% (w/w) quaternary ammonium biocide. The cleansing composition is substantially free of a betaine-based surfactant and substantially free of a compound selected from the group consisting of triclosan, triclocarban, a halogenated phenolic antimicrobial agent, and combinations thereof.

In another aspect, the present disclosure is directed to an antimicrobial cleansing gel composition including a polar carrier solvent, a cationic compatible surfactant, a quaternary ammonium biocide, a cationic compatible afterfeel agent, and a cationic compatible thickening agent. The cleansing composition includes from about 0.1% (w/w) to about 15% (w/w) cationic compatible surfactant and from about 0.01% (w/w) to about 10% (w/w) quaternary ammonium biocide. The cleansing composition is substantially free of a betaine-based surfactant and substantially free of a compound selected from the group consisting of triclosan, triclocarban, a halogenated phenolic antimicrobial agent, and combinations thereof.

In yet another aspect, the present disclosure is directed to an antimicrobial cleansing composition including a polar carrier solvent, a cationic compatible surfactant, a quaternary ammonium biocide, and a cationic compatible afterfeel agent. The cleansing composition includes from about 1.0% (w/w) cationic compatible surfactant and from about 0.01% (w/w) to about 10% (w/w) quaternary ammonium biocide. The cleansing composition is completely free of a betaine-based surfactant and completely free of a compound selected from the group consisting of triclosan, triclocarban, a halogenated phenolic antimicrobial agent, and combinations thereof.

In another aspect, the present disclosure is directed to an antimicrobial cleansing gel composition including a polar carrier solvent, a cationic compatible surfactant, a quaternary ammonium biocide, a cationic compatible afterfeel agent, and a cationic compatible thickening agent. The cleansing composition includes from about 0.1% (w/w) to about 15% (w/w) cationic compatible surfactant and from about 0.01% (w/w) to about 10% (w/w) quaternary ammonium biocide. The cleansing gel composition is completely free of a betaine-based surfactant and completely free of a compound selected from the group consisting of triclosan, triclocarban, a halogenated phenolic antimicrobial agent, and combinations thereof.

In one aspect, the present disclosure is directed to an antimicrobial cleansing composition including a polar carrier solvent, a cationic compatible surfactant, a quaternary ammonium biocide, and a cationic compatible afterfeel agent. The cleansing composition includes from about 0.1% (w/w) to about 15% (w/w) cationic compatible surfactant and from about 0.01% (w/w) to about 10% (w/w) quaternary ammonium biocide. The cleansing composition is substantially free of a betaine-based surfactant and completely free of a compound selected from the group consisting of triclosan, triclocarban, a halogenated phenolic antimicrobial agent, and combinations thereof.

In one aspect, the present disclosure is directed to an antimicrobial cleansing composition including a polar carrier solvent, a cationic compatible surfactant, a quaternary ammonium biocide, and a cationic compatible afterfeel agent. The cleansing composition includes from about 0.1% (w/w) to about 15% (w/w) cationic compatible surfactant and from about 0.01% (w/w) to about 10% (w/w) quaternary ammonium biocide. The cleansing composition is completely free of a betaine-based surfactant and substantially free of a compound selected from the group consisting of triclosan, triclocarban, a halogenated phenolic antimicrobial agent, and combinations thereof.

In one aspect, the present disclosure is directed to an antimicrobial cleansing gel composition including a polar carrier solvent, a cationic compatible surfactant, a quaternary ammonium biocide, and a cationic compatible afterfeel agent. The cleansing composition includes from about 0.1% (w/w) to about 15% (w/w) cationic compatible surfactant and from about 0.01% (w/w) to about 10% (w/w) quaternary ammonium biocide. The cleansing composition is substantially free of a betaine-based surfactant and completely free of a compound selected from the group consisting of triclosan, triclocarban, a halogenated phenolic antimicrobial agent, and combinations thereof.

In one aspect, the present disclosure is directed to an antimicrobial cleansing gel composition including a polar carrier solvent, a cationic compatible surfactant, a quaternary ammonium biocide, and a cationic compatible afterfeel agent. The cleansing composition includes from about 0.1% (w/w) to about 15% (w/w) cationic compatible surfactant and from about 0.01% (w/w) to about 10% (w/w) quaternary ammonium biocide. The cleansing composition is completely free of a betaine-based surfactant and substantially free of a compound selected from the group consisting of triclosan, triclocarban, a halogenated phenolic antimicrobial agent, and combinations thereof.

DETAILED DESCRIPTION

The present disclosure is directed to antimicrobial cleansing compositions that are safe and effective for everyday use in that they do not contain potentially environmentally dangerous ingredients. The antimicrobial cleansing compositions include quaternary ammonium biocides as the primary active antimicrobial ingredients. These and other essential or optional elements or limitations of the cleansing compositions of the present disclosure are described in detail hereinafter.

As used herein, the term "cationic compatible" refers to a compound such as an afterfeel agent or a thickening agent that does not interfere with or inhibit the antimicrobial activity of the quaternary ammonium biocide. Further, the "cationic compatible afterfeel agents" and "cationic compatible thickening agents" do not compromise the stability of the antimicrobial cleansing composition. As used herein the phrase "compromise the stability" refers to interfering with the physical stability and overall structure of the antimicrobial cleansing composition. By way of example, anionic thickeners and surfactants compromise the stability of the antimicrobial cleansing composition by forming coacervates with the cationic quaternary ammonium biocide. Additionally, certain non-ionic surfactants inactivate the efficacy of the cationic quaternary ammonium biocide by forming complex micellular structures, thus compromising the composition.

As used herein, the term "substantially free" refers to the composition including less than a functional amount of an ingredient, typically less than 1.0% by weight, and more suitably less than 0.3% by weight. In particularly suitable embodiments, the compositions are completely free; that is, include zero percent by weight, of such optional or selected essential ingredients.

Unless defined otherwise, all other technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Antimicrobial Cleansing Compositions

The present disclosure is directed to an antimicrobial cleansing composition. In one aspect, the antimicrobial cleansing composition is in the form of a thin liquid or foaming antimicrobial cleansing composition. In yet another aspect, the antimicrobial cleansing composition is in the form of an antimicrobial cleansing gel composition.

The antimicrobial cleansing compositions of the present disclosure include a polar carrier solvent, a quaternary ammonium biocide, a cationic compatible surfactant, and a cationic compatible afterfeel agent.

Suitable polar carrier solvents include those being compatible with water. As used herein, "compatible with water" refers to the polar carrier solvent being soluble in water such as to have a degree of solubility in water at room temperature of at least about 75%, including from about 80% to 100%, including from about 90% to 100%, and including from about 95% to 100%. In one particularly suitable embodiment, the polar carrier solvent is completely soluble in water; that is, is 100% soluble in water at room temperature.

It should be recognized by one skilled in the art that the polar carrier solvent can be any suitable solvent being compatible with water as known in the art and that further does not negatively impact the foaming properties of the antimicrobial cleansing composition.

Suitable polar carrier solvents may include, for example, water, glycerin, propylene glycol, butylene glycol, polyethylene glycol, and combinations thereof. Suitable amounts of polar carrier solvent in the antimicrobial cleansing composition may be from at least about 60% (w/w), including from about 65%(w/w) to about 95%(w/w), and including from about 70%(w/w) to about 90%(w/w).

The antimicrobial cleansing composition further includes at least one quaternary ammonium biocide. Quaternary ammonium biocides are a specific sub-class of cationic surfactants where the positive charge comes from a quaternized nitrogen. Quaternary ammonium cations, also known as "quats", are positively charged polyatomic ions of the structure $NR_4^+$ with R corresponding to alkyl, aryl, and benzyl groups or the combinations of these groups. Unlike the ammonium ion $HNR_3^+$ itself (and primary, secondary, or tertiary ammonium cations), quaternary ammonium cations are permanently charged, independent of the pH of their solution. Quaternary ammonium cations may be synthesized by alkylation, arylation, or benzylation of ammonia or other amines. The quaternary ammonium biocides for use in the present antimicrobial cleansing compositions are non-carcinogenic.

Suitable quaternary ammonium biocides include those having efficacy against microbes, including, for example, benzalkonium chloride, benzethonium chloride, didecyldimonium chloride, dioctyldimonium chloride, and combinations thereof.

Suitable amounts of the quaternary ammonium biocide in the antimicrobial cleansing composition may be from about 0.01% (w/w) to about 10% (w/w), including from about 0.025% (w/w) to about 2.5% (w/w), and including from about 0.05% (w/w) to about 1.25% (w/w).

Further antimicrobial active ingredients, in addition to the quaternary ammonium biocides, may be used in the antimicrobial cleansing compositions. The additional antimicrobial active ingredients should be compatible with the quaternary ammonium biocide, and thus, should not interfere with or inhibit the antimicrobial activity of the quaternary ammonium biocide. Specific examples include chlorhexidine gluconate also known as CHG, chlorhexidine acetate, poly(hexamethylene biguanide) also known as PHMB.

The antimicrobial cleansing compositions further include at least one cationic compatible surfactant. Suitable cationic compatible surfactants include, for example, cationic surfactants, amine oxide surfactants, and combinations thereof. More particularly, suitable cationic compatible surfactants may include, for example, cationic amines such as, for example, cetrimonium chloride, stearalkonium chloride, behentrimonium methosulfate, amine salts such as, for example, isostearamidopropyl morpholine lactate, and stearamidopropyl dimethylamine lactate, linoleamidopropyl PG dimonium chloride, undecyleneamidopropyltrimonium methosulfate, and other salts thereof, and combinations thereof.

Suitably, the antimicrobial cleansing compositions include from about 0.1% (w/w) to about 15% (w/w), including from about 0.2% (w/w) to about 10% (w/w), and including from about 0.5% (w/w) to about 8% (w/w), of a cationic compatible surfactant.

The antimicrobial cleansing compositions of the present disclosure should be substantially free, and suitably, completely free (i.e., contain zero percent by weight), of non-ionic surfactants, anionic surfactants, and betaine-based surfactants. As commonly understood by one of ordinary skill in the art, non-ionic surfactants have long been known to neutralize the antimicrobial activity of quaternary ammonium biocides. Additionally, the antimicrobial cleansing compositions are substantially free, and suitably, completely free (i.e., contain zero percent by weight) of triclosan, triclocarban, and other halogenated phenolic antimicrobial agents.

Additionally, the antimicrobial cleansing compositions include a cationic compatible afterfeel agent. It has been unexpectedly found that the addition of various afterfeel agents in the antimicrobial cleansing compositions mitigates the tacky, heavy after-feel caused by the quaternary ammonium biocides. Particularly suitable cationic compatible afterfeel agents may be, for example, cationic compatible polymers. This is particularly unexpected as the substantive nature of cationic compatible polymers would be expected to make the composition feel even more tacky and heavy on the skin.

Suitable cationic compatible polymers may be, for example, those having a permanent positive charge. Suitable polymers having a permanent positive charge may be, for example, polyquaternium-47, polymethacrylamidopropyltrimonium chloride, polyquaternium-7, polyquaternium-15, polyquaternium-2, and combinations thereof.

Additionally suitable compounds for use as the cationic compatible afterfeel agent include nonionic polymers such as polysilicone-20, di-PPG-2 myreth-10 adipate, PEG-12, PEG-7 glyceryl cocoate, and the like, and combinations thereof.

Suitable amounts of cationic compatible afterfeel agents in the antimicrobial cleansing composition of the present disclosure include from about 0.1 (w/w) to about 12% (w/w), including from about 0.1% (w/w) to about 10% (w/w).

As described above, in one aspect of the present disclosure, the antimicrobial cleansing composition is directed to an antimicrobial cleansing gel composition. When the antimicrobial cleansing composition is a gel composition, the cleansing composition further includes a cationic compatible thickening agent.

It has been unexpectedly found that the antimicrobial cleansing gel composition of the present disclosure can be thickened while at the same time not affecting the antimicrobial efficacy of the quaternary ammonium biocide. The cationic compatible thickening agent provides a suitable viscosity to the antimicrobial cleansing gel composition in the range of about 1000 centipoise to about 30000 centipoise. A more suitable viscosity of the antimicrobial cleansing gel composition may be a viscosity ranging from about 1000 centipoise to about 20000 centipoise.

Suitable cationic compatible thickening agents may be, for example, uncharged polymers, cationic polymers, and combinations thereof. Suitable uncharged polymeric thickening agents may be, for example, high molecular weight, non-foaming polyethylene glycol esters such as, for example, polyethylene glycol (PEG)-175 diisostearate, PEG-175 distearate, PEG-150 distearate, PEG-90 diisostearate, and combinations thereof. Other suitable uncharged polymeric thickening agents include, for example, Polyether-1, PEG-100 isophorone diisocyanate (IPDI) Copolymer, PEG-75 IPDI Copolymer, PEG-180/Laureth-50/tetramethoxymethylglycouril (TMMG) Copolymer, PEG-180/Octoxynol-40/TMMG Copolymer, and combinations thereof. Suitable cationic polymeric thickening agents include, for example, Polyacrylate-1 Crosspolymer, and derivatives thereof.

Suitable amounts of the cationic compatible thickening agent in the antimicrobial cleansing gel composition may be from about 0.5% to about 15%, including from about 0.75% to about 10%, and including from about 1.0% to about 8%.

In addition to the ingredients described above, the antimicrobial cleansing composition may further include optional ingredients such as, for example, vitamins, botanical compounds, moisturizers, and combinations thereof.

Suitable vitamins may be, for example, Vitamins A, B, C, D, E, the associated variants (e.g., B2, B3, B4, B5, B6, B7, D2, and D3), and the associated derivatives (Vitamin A Palmitate, Vitamin E Acetate).

As used herein, the term "botanical compound" is meant to include bio-compounds such as botanical extracts and/or botanical actives, as well as essential oils and herbs. Suitable botanical compounds include Aloe Ferox HS, American Ginseng, Calendula (Marigold), Comfey Leaves, Cromoist 0-25, Cromoist HYA, Dandelion, Devil's Claw, Dong Quai, Echinacea Dry Aq., Gingko Biloba, Ginseng GR 471 Hydro, Glucosamine 99, Goldenseal, Gotu Kola PG 5:1, Grape Seed Extract, Green Tea, Hydrolite-5, Hydrosoy 2000 SF, Marron D'Inde (Horse Chestnut), Milk Thistle, Nab Willowbark Extr., Soluble Wheat Protein, Spirulina, St. John's Wort W/S, White Mistle Toe, Witchhazel Distillate, Witchhazel GW, Yucca 70, and Yucca Extr. Powder 50%.

Suitable moisturizers may be, for example, glycerin, betaine, hydroxyethyl urea; urea; PCA and salts of PCA (Na, Mg, Mn, Cu, Arginine, etc), Sodium Lactate, Potassium Lactate, and combinations thereof.

The antimicrobial cleansing compositions of the present disclosure exist as a single phase, completely soluble system. The ingredients and formulations further result in stable compositions with antimicrobial efficacy.

The disclosure will be more fully understood upon consideration of the following non-limiting Examples.

EXAMPLES

Example 1

In this Example, the impact of cocamidopropyl betaine (CAPB) on the antimicrobial activity of cationic biocides against *E. coli* K12 (ATCC 29425) was analyzed.

Specifically, *E. coli* K12 was contacted for 60 seconds in a 0.3 g/L solution of bovine serum albumin mixed with a solution containing a cationic biocide, with or without CAPB (3.5% w/w active). As shown in Table 1, antimicrobial activity was reduced to less than 3.1 ($LOG_{10}$ CFU/ml) in the presence of CAPB.

TABLE 1

Impact of CAPB on Cationic Biocides.
$LOG_{10}$ CFU/ml Reduction

| Actives (all 0.3% active) | w/o CAPB | w/ CAPB |
|---|---|---|
| Benzalkonium chloride | >5.5 | <3.1 |
| Benzethonium chloride | >5.5 | <3.1 |
| Didecyldimonium chloride | 4.5 | <3.1 |
| Chlorhexidine gluconate | 5.5 | <3.1 |

Example 2

In this Example, the impact of cocamidopropyl betaine (CAPB) on the antimicrobial activity of cationic biocides against *P. aeruginosa* (ATCC 15442) was analyzed.

Specifically, *P. aeruginosa* was contacted for 60 seconds in a 0.3 g/L solution of bovine serum albumin and mixed with a solution containing a cationic biocide, with or without CAPB (3.5% w/w active). As shown in Table 2, antimicrobial activity was reduced to less than 3.3 ($LOG_{10}$ CFU/ml) in the presence of CAPB.

TABLE 2

Impact of CAPB on Cationic Biocides.
$LOG_{10}$ CFU/ml Reduction

| Actives (all 0.3% active) | w/o CAPB | w/ CAPB |
|---|---|---|
| Benzalkonium chloride | >5.7 | <3.3 |
| Benzethonium chloride | >5.7 | <3.3 |
| Didecyldimonium chloride | >5.7 | <3.3 |
| Chlorhexidine gluconate | >5.7 | <3.3 |

Example 3

In this Example, the impact of cocamidopropyl betaine (CAPB) on the antimicrobial activity of cationic biocides against *S. aureus* (ATCC 6538) was analyzed.

Specifically, *S. aureus* was contacted for 60 seconds in a 0.3 g/L solution of bovine serum albumin mixed with a solution containing a cationic biocide, with or without CAPB (3.5% w/w active). As shown in Table 3, antimicrobial activity was reduced to less than 2.4 ($LOG_{10}$ CFU/ml) for benzalkonium chloride, benzethonium chloride and chlorhexidine gluconate and to 4.0 $LOG_{10}$ CFU/ml for didecyldimonium chloride in the presence of CAPB.

TABLE 3

Impact of CAPB on Cationic Biocides.
$LOG_{10}$ CFU/ml Reduction

| Actives (all 0.3% active) | w/o CAPB | w/ CAPB |
|---|---|---|
| Benzalkonium chloride | >4.9 | <2.4 |
| Benzethonium chloride | >4.9 | <2.4 |
| Didecyldimonium chloride | >4.9 | 4 |
| Chlorhexidine gluconate | 3.2 | <2.4 |

Example 4

In this Example, the impact of cocamidopropyl betaine (CAPB) on the antimicrobial activity of cationic biocides against *E. faecalis* (ATCC 29212) was analyzed.

Specifically, *E. faecalis* was contacted for 60 seconds in a 0.3 g/L solution of bovine serum albumin mixed with a solution containing a cationic biocide, with or without CAPB (3.5% w/w active). As shown in Table 4, antimicrobial activity was reduced to less than 3.3 ($LOG_{10}$ CFU/ml) for benzalkonium chloride, benzethonium chloride and didecyldimonium chloride in the presence of CAPB.

TABLE 4

Impact of CAPB on Cationic Biocides.
$LOG_{10}$ CFU/ml Reduction

| Actives (all 0.3% active) | w/o CAPB | w/ CAPB |
|---|---|---|
| Benzalkonium chloride | >5.7 | <3.3 |
| Benzethonium chloride | 4.8 | <3.3 |
| Didecyldimonium chloride | >5.7 | <3.3 |
| Chlorhexidine gluconate | <3.3 | <3.3 |

Example 5

In this Example, the impact of other betaine-based surfactants on the antimicrobial activity of benzalkonium chloride against *E. coli* K12 (ATCC 29425) was analyzed.

Specifically, *E. coli* K12 was contacted for 60 seconds in a 0.3 g/L solution of bovine serum albumin mixed with a solution containing benzalkonium chloride, with or without a betaine-based surfactant (3.5% w/w active). As shown in Table 5, antimicrobial activity was reduced to less than 3.1 ($LOG_{10}$ CFU/ml) when benzalkonium chloride was combined with a betaine-based surfactant.

TABLE 5

Impact of other betaine-based surfactants on benzalkonium chloride efficacy against *E. coli* K12. Concentrations represent percent activity.
$LOG_{10}$ CFU/ml Reduction

| Surfactant | 0.3% benzalkonium chloride | 0.3% benzalkonium chloride + 3.5% surfactant |
|---|---|---|
| Lauramidopropyl betaine | >5.5 | <3.0 |
| Meadowfoamamidopropyl betaine | | <3.0 |
| Coco-betaine | | <3.1 |
| Lauryl betaine | | <3.1 |

Example 6

In this Example, the impact of cocamidopropyl betaine (CAPB) on the in vivo antimicrobial activity of a didecyldimonium chloride foam cleansing composition against *E. coli* K12 (ATCC 29425) was analyzed.

Specifically, two didecyldimonium chloride foam cleansing compositions (Formulations 1 and 2) were analyzed according to the EN1499 standard. Formulations 1 and 2 were equivalent with the exception of the type of surfactant used. The overall level of surfactant remained constant. Formulation 1 included cocamidopropyl betaine whereas Formulation 2 included other non-betaine-based surfactants (see Table 6). An equivalent volume of each formulation was applied to the hands of subjects and used to wash for 60 seconds. The $LOG_{10}$ number of *E. coli* K12 remaining on the hands following washing was compared to the $LOG_{10}$ number on hands prior to washing. The Formulation 2 cleansing composition, not containing a betaine-based surfactant, provided a significantly larger $LOG_{10}$ reduction than the Formulation 1 cleansing composition containing CAPB (student's t-test, 99% confidence interval) (see Table 7).

TABLE 6

| | INCI Name | Percent Active |
|---|---|---|
| Formulation 1 | Water | 92.62 |
| | Didecyldimonium Chloride | 0.88 |
| | Cocamidopropyl Betaine | 2.80 |
| | Di-PPG-2 Myreth-10 Adipate | 1.00 |
| | Polysilicone-20 | 2.00 |
| | Polyaminopropyl Biguanide | 0.10 |
| | Polymethacrylamidopropyltrimonium Chloride | 0.50 |
| | Tetrasodium Iminodisuccinic Acid | 0.10 |
| | Citric Acid | 0.00 |
| | | 100.00 |
| | Final pH | 4.55 |
| Formulation 2 | Water | 92.54 |
| | Didecyldimonium Chloride | 0.88 |
| | Cetrimonium Chloride | 0.95 |
| | Cocoamidopropylamine Oxide | 0.95 |
| | Myristamine Oxide | 0.95 |
| | Di-PPG-2 Myreth-10 Adipate | 1.00 |
| | Polysilicone-20 | 2.00 |
| | Polyaminopropyl Biguanide | 0.10 |
| | Polymethacrylamidopropyltrimonium Chloride | 0.50 |
| | Tetrasodium Iminodisuccinic Acid | 0.10 |
| | Citric Acid | 0.03 |
| | | 100.00 |
| | Final pH | 6.10 |

TABLE 7

Impact of surfactant selection on the in vivo efficacy of benzalkonium chloride foam formulations against *E. coli* K12 according to methods described in the EN 1499 standard.

| Formulation | $LOG_{10}$ prevalue | $LOG_{10}$ postvalue | $LOG_{10}$ reduction |
|---|---|---|---|
| Formulation 1 | 6.5 | 3.6 | 2.9 |
| Formulation 2 | 6.5 | 2.9 | 3.6* |

*Significantly larger $LOG_{10}$ reduction compared to that observed with Formulation 1, student's t-test, 99% confidence interval In view of the above, it will be seen that the several advantages of the disclosure are achieved and other advantageous results attained. As various changes could be made in the above components without departing from the scope of the disclosure, it is intended that all matter contained in the above description shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An antimicrobial cleansing composition comprising:
   a polar carrier solvent;
   from about 0.1% (w/w) to about 15% (w/w) cationic compatible surfactant;
   from about 0.01% (w/w) to about 10% (w/w) quaternary ammonium biocide; and
   a cationic compatible afterfeel agent, wherein the antimicrobial cleansing composition is substantially free of a betaine-based surfactant and substantially free of a compound selected from the group consisting of triclosan, triclocarban, a halogenated phenolic antimicrobial agent, and combinations thereof.

2. The antimicrobial cleansing composition of claim 1, wherein the polar carrier solvent is selected from the group consisting of water, glycerin, propylene glycol, butylene glycol, polyethylene glycol, and combinations thereof.

3. The antimicrobial cleansing composition of claim 1, wherein the cleansing composition comprises from about 60%(w/w) to about 95%(w/w) polar carrier solvent.

4. The antimicrobial cleansing composition of claim 1, wherein the quaternary ammonium biocide is selected from the group consisting of benzalkonium chloride, benzethonium chloride, didecyldimonium chloride, dioctyldimonium chloride, and combinations thereof.

5. The antimicrobial cleansing composition of claim 1, wherein the afterfeel agent is selected from the group consisting of di-PPG-2-myreth-10 adipate, polysilicone-20, polymethacrylamidopropyltrimonium chloride, polyquaternium-7, polyquaternium-15, polyquaternium-2, and combinations thereof.

6. The antimicrobial cleansing composition of claim 1, wherein the cleansing composition comprises from about 0.1% (w/w) to about 5% (w/w) afterfeel agent.

7. The antimicrobial cleansing composition of claim 1, wherein the cleansing composition is substantially free of a non-ionic surfactant.

8. The antimicrobial cleansing composition of claim 1 further comprising at least one of vitamins, botanical compounds, and moisturizers.

9. An antimicrobial cleansing gel composition comprising:
   a polar carrier solvent;
   from about 1.0% (w/w) to about 15% (w/w) cationic compatible surfactant;
   from about 0.01% (w/w) to about 10% (w/w) quaternary ammonium biocide;
   a cationic compatible afterfeel agent; and
   a cationic compatible thickening agent, wherein the antimicrobial cleansing gel composition is substantially free of a betaine-based surfactant and substantially free of a compound selected from the group consisting of triclosan, triclocarban, a halogenated phenolic antimicrobial agent, and combinations thereof.

10. The antimicrobial cleansing gel composition of claim 9, wherein the polar carrier solvent is selected from the group consisting of water, glycerin, propylene glycol, butylene glycol, polyethylene glycol, and combinations thereof.

11. The antimicrobial cleansing gel composition of claim 9, wherein the cleansing gel composition comprises from about 60% (w/w) to about 95% (w/w) polar carrier solvent.

12. The antimicrobial cleansing gel composition of claim 9, wherein the quaternary ammonium biocide is selected from the group consisting of benzalkonium chloride, benzethonium chloride, didecyldimonium chloride, dioctyldimonium chloride, and combinations thereof.

13. The antimicrobial cleansing gel composition of claim 9, wherein the afterfeel agent is selected from the group consisting of di-PPG-2-myreth-10 adipate, polysilicone-20, polymethacrylamidopropyltrimonium chloride, polyquaternium-7, polyquaternium-15, polyquaternium-2, and combinations thereof.

14. The antimicrobial cleansing gel composition of claim 9, wherein the cleansing gel composition comprises from about 0.1% (w/w) to about 12% (w/w) afterfeel agent.

15. The antimicrobial cleansing gel composition of claim 9, wherein the cationic compatible thickening agent is selected from the group consisting of a non-ionic thickening agent, a cationic thickening agent, a cationic compatible polymer, and combinations thereof.

16. The antimicrobial cleansing gel composition of claim 9, wherein the cleansing gel composition is substantially free of a non-ionic surfactant.

17. The antimicrobial cleansing gel composition of claim 9 further comprising at least one of vitamins, botanical compounds, and moisturizers.

18. An antimicrobial cleansing composition comprising:
a polar carrier solvent;
from about 0.1% (w/w) to about 15% (w/w) cationic compatible surfactant;
from about 0.01% (w/w) to about 10% (w/w) quaternary ammonium biocide;
a cationic compatible afterfeel agent; and
wherein the antimicrobial cleansing composition is completely free of a betaine-based surfactant and completely free of a compound selected from the group consisting of triclosan, triclocarban, a halogenated phenolic antimicrobial agent, and combinations thereof.

19. The antimicrobial cleansing composition of claim 18, wherein the quaternary ammonium biocide is selected from the group consisting of benzalkonium chloride, benzethonium chloride, didecyldimonium chloride, dioctyldimonium chloride, and combinations thereof.

20. The antimicrobial cleansing composition of claim 18, wherein the afterfeel agent is selected from the group consisting of di-PPG-2-myreth-10 adipate, polysilicone-20, polymethacrylamidopropyltrimonium chloride, polyquaternium-7, polyquaternium-15, polyquaternium-2, and combinations thereof.

21. An antimicrobial cleansing composition comprising:
a polar carrier solvent;
from about 0.1% (w/w) to about 15% (w/w) cationic compatible surfactant selected from the group consisting of amine oxide surfactants, cetrimonium chloride, stearalkonium chloride, behentrimonium methosulfate, isostearamidopropyl morpholine lactate, stearamidopropyl dimethylamine lactate, linoleamidopropyl PG dimonium chloride, undecyleneamidopropyltrimonium methosulfate, and salts thereof, and combinations thereof;
from about 0.01% (w/w) to about 10% (w/w) quaternary ammonium biocide; and
a cationic compatible afterfeel agent, wherein the antimicrobial cleansing composition is substantially free of a betaine-based surfactant and substantially free of a compound selected from the group consisting of triclosan, triclocarban, a halogenated phenolic antimicrobial agent, and combinations thereof.

22. The antimicrobial cleansing composition of claim 21 wherein the quaternary ammonium biocide is selected from the group consisting of benzalkonium chloride, benzethonium chloride, didecyldimonium chloride, dioctyldimonium chloride, and combinations thereof.

23. The antimicrobial cleansing composition of claim 21 wherein the amine oxide is selected from the group consisting of cocoamidopropylamine oxide and myristamine oxide.

* * * * *